United States Patent
Lynch

(10) Patent No.: US 9,801,990 B2
(45) Date of Patent: Oct. 31, 2017

(54) PUMP CLEAN-OUT SYSTEM

(71) Applicant: RELIANTHEART INC., Houston, TX (US)

(72) Inventor: Bryan E. Lynch, Houston, TX (US)

(73) Assignee: RELIANTHEART INC., Houston, TX (US)

( * ) Notice: Subject to any disclaimer, the term of this patent is extended or adjusted under 35 U.S.C. 154(b) by 0 days.

(21) Appl. No.: 14/574,612

(22) Filed: Dec. 18, 2014

(65) Prior Publication Data

US 2015/0165103 A1 Jun. 18, 2015

Related U.S. Application Data

(62) Division of application No. 13/591,053, filed on Aug. 21, 2012, now Pat. No. 8,961,698.

(60) Provisional application No. 61/525,825, filed on Aug. 21, 2011.

(51) Int. Cl.
*A61M 1/12* (2006.01)
*A61M 1/10* (2006.01)
*B08B 9/032* (2006.01)

(52) U.S. Cl.
CPC ............ *A61M 1/122* (2014.02); *A61M 1/101* (2013.01); *B08B 9/032* (2013.01)

(58) Field of Classification Search
CPC ........ A61M 1/10; A61M 1/101; A61M 1/122; B08B 9/032
See application file for complete search history.

(56) References Cited

U.S. PATENT DOCUMENTS

| | | | |
|---|---|---|---|
| 5,527,159 A | 6/1996 | Bozeman, Jr. et al. | |
| 6,183,412 B1 | 2/2001 | Benkowski et al. | |
| 6,422,990 B1 | 7/2002 | Prem | |
| 7,753,115 B2 | 7/2010 | Zupanick | |
| 2003/0040704 A1* | 2/2003 | Dorros | A61B 17/12109 604/101.04 |
| 2009/0143635 A1 | 6/2009 | Benkowski et al. | |
| 2009/0221949 A1* | 9/2009 | Allers | A61M 1/3621 604/6.16 |
| 2012/0031430 A1 | 2/2012 | Thykjaer | |

* cited by examiner

*Primary Examiner* — Tatyana Zalukaeva
*Assistant Examiner* — Benjamin Klein
(74) *Attorney, Agent, or Firm* — Sutton McAughan Deaver PLLC

(57) ABSTRACT

A system for cleaning an implanted blood pump, comprising: an inflow catheter having an expandable inflow member positioned about the periphery thereof; an inflow tube coupled with the inflow catheter; a valve assembly coupled to the inflow tube; an outflow tube coupled to the valve assembly; and an outflow catheter having an expandable outflow member positioned about the periphery thereof, the outflow catheter being coupled to the outflow tube. In use, the inflow tube and outflow tube extend through the skin of a human body, the inflow catheter and outflow catheter are positioned within the human body, and the valve assembly is positioned outside the human body.

18 Claims, 2 Drawing Sheets

PUMP CLEAN-OUT SYSTEM

CROSS REFERENCE TO RELATED APPLICATIONS

This application claims priority to, and is a divisional of U.S. application Ser. No. 13/591,053, filed Aug. 21, 2012, entitled "Pump Clean-Out System" and the benefit of U.S. Ser. No. 61/525,825, filed Aug. 21, 2011, entitled "Clean-Out System for Heart Pump", both of which are incorporated herein by specific reference.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The inventions disclosed and taught herein relate generally to fluid pumps; and more specifically relate to blood pumps for implantation and use to replace and/or supplement a heart.

Description of the Related Art

U.S. Pat. No. 5,527,159 discloses a "rotary blood pump includes a pump housing for receiving a flow straightener, a rotor mounted on rotor bearings and having an inducer portion and an impeller portion, and a diffuser. The entrance angle, outlet angle, axial and radial clearances of blades associated with the flow straightener, inducer portion, impeller portion and diffuser are optimized to minimize hemolysis while maintaining pump efficiency. The rotor bearing includes a bearing chamber that is filled with cross-linked blood or other bio-compatible material. A back emf integrated circuit regulates rotor operation and a microcomputer may be used to control one or more back emf integrated circuits. A plurality of magnets are disposed in each of a plurality of impeller blades with a small air gap. A stator may be axially adjusted on the pump housing to absorb bearing load and maximize pump efficiency."

U.S. Pat. No. 6,183,412 discloses a "controller module for an implantable pump system which has a pump motor includes a processor, a motor controller electrically coupled to the processor and adapted to power the pump motor such that the pump motor operates at a desired speed. The motor controller outputs digital representations of the pump motor operating parameters to the processor. A first memory device is coupled to the processor for storing the digital signals representing the pump motor operating parameters. The controller module further includes a user interface. The controller module may be coupled to a data acquisition system, which provides power and exchanges data with the controller module. The controller module may alternately be coupled to a home support system which provides power for the controller module and storage for system components."

U.S. Patent Application Publication No. discloses 20090143635 a "blood pump consisting of an inflow cannula, a stator fixed to the pump housing, a flow straightener, an impeller, and a diffuser. The pump may include a flow straightener assembly consisting of the flow straightener body and front shaft. The pump may include an impeller assembly with a bearing on the front hub section. The pump may have a body contour which is shaped such that the rear section of the flow straightener body blends into the inserted shaft and there is no axial gap between the end of the flow straightener other than the ends of the blades and the front hub of the impeller."

The inventions disclosed and taught herein are directed to a system and method for cleaning out a pump, such as an implanted blood pump.

BRIEF SUMMARY OF THE INVENTION

A system for cleaning an implanted blood pump, comprising: an inflow catheter having an expandable inflow member positioned about the periphery thereof; an inflow tube coupled with the inflow catheter; a valve assembly coupled to the inflow tube; an outflow tube coupled to the valve assembly; and an outflow catheter having an expandable outflow member positioned about the periphery thereof, the outflow catheter being coupled to the outflow tube. The expandable members selectively expand outwardly from the catheter and form a seal between the catheter and a cannula of the implanted blood pump. When expanded, the expandable members preferably form a conical distal end defined by a conical interior portion. For example, the expandable members may essentially be balloons that are selectively inflated and deflated through a lumen, which may be integrated with the respective tubes to form dual lumens. In use, the tubes and/or lumens pass through the skin of a human body, with the catheters positioned within the human body and the valve assembly positioned outside the human body. This allows the present invention to clean out the implanted blood pump without removing the pump from the patient.

A method of cleaning an implanted blood pump, the method comprising the steps of: inserting an inflow catheter into an inflow cannula of the implanted pump; expanding an expandable inflow member, thereby creating a seal between the inflow catheter and inflow cannula; inserting an outflow catheter into an outflow cannula of the implanted pump; expanding an expandable outflow member, thereby creating a seal between the outflow catheter and outflow cannula; flushing the implanted pump; collapsing the expandable members; and removing the catheters. These steps are preferably performed while the implanted pump is implanted within a human body. The flushing step may comprise flushing the implanted pump with a rinsing fluid; flushing the implanted pump with a thrombolytic fluid; and flushing the implanted pump with the rinsing fluid. The flushing step may comprise allowing the thrombolytic fluid to dwell in the implanted pump and/or agitating the thrombolytic fluid within the implanted pump. Expanding the expandable members comprise causing a distal end thereof to extend distally and outwardly from the catheter, thereby forming a conical interior portion. This conical interior portion of the distal end of the catheter/expandable member assembly collects debris from cleaned from the pump and prevents such debris from being trapped between the expandable member and the cannula.

DETAILED DESCRIPTION OF THE INVENTION

Figure 1:
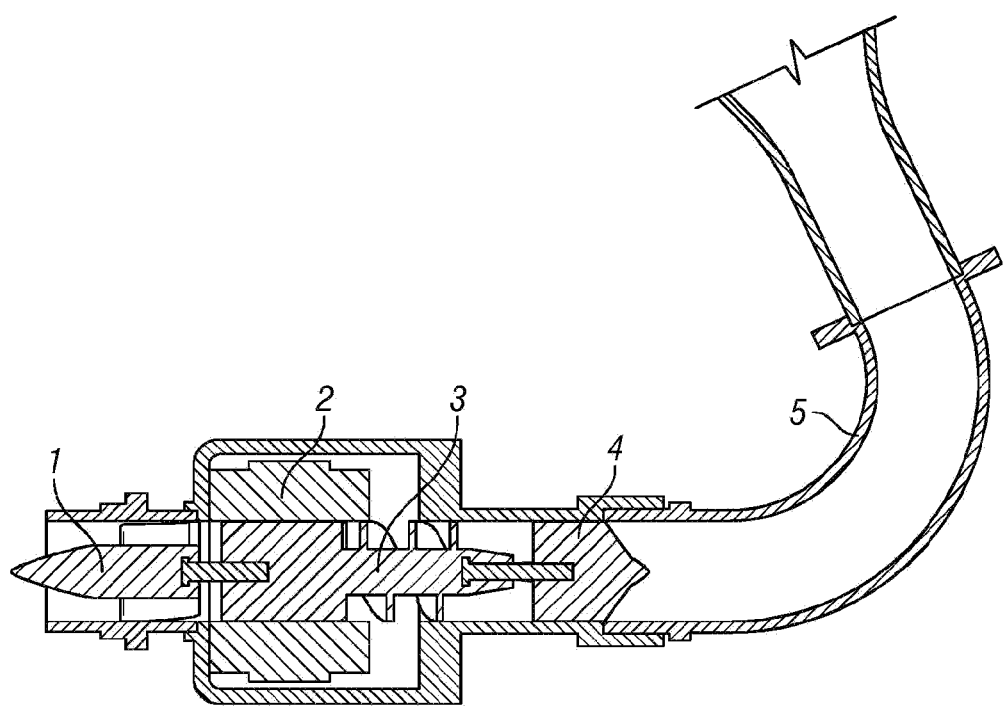
FIG. 1 illustrates pump assembly for which the present invention may be particularly useful.

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

For all purposes of this disclosure, the entire subject matter of the following published applications and patents are incorporated by reference as if fully reprinted herein: U.S. Pat. No. 5,527,159; U.S. Pat. No. 5,947,892; U.S. Pat. No. 6,183,412; U.S. Pat. No. 7,175,588; U.S Patent Application Publication No. 200410215050; U.S Patent Application Publication No. 200510131271; U.S Patent Application Publication No. 200610241335; and U.S. Patent Application Publication No. 20090143635.

Applicants have created a system and method to clean out the interior of such pump, such as an implantable blood pump, without removing the pump. The system for cleaning an implanted blood pump, according to the present invention, preferably comprises: an inflow catheter having an expandable inflow member positioned about the periphery thereof; an inflow tube coupled with the inflow catheter; a valve assembly coupled to the inflow tube; an outflow tube coupled to the valve assembly; and an outflow catheter having an expandable outflow member positioned about the periphery thereof, the outflow catheter being coupled to the outflow tube. The expandable members selectively expand outwardly from the catheter to form a seal between the catheter and a cannula of the implanted blood pump. When expanded, the expandable members preferably form a conical distal end defined by a conical interior portion. For example, the expandable members may essentially be balloons that are selectively inflated and deflated through a lumen, which may be integrated with the respective tubes to form dual lumens. In use, the tubes and/or lumens pass through the skin of a human body, with the catheters positioned within the human body and the valve assembly positioned outside the human body. This allows the present invention to clean out the implanted blood pump without removing the pump from the patient.

The method of cleaning an implanted blood pump, according to the present invention, preferably comprises the steps of: inserting an inflow catheter into an inflow cannula of the implanted pump; expanding an expandable inflow member, thereby creating a seal between the inflow catheter and inflow cannula; inserting an outflow catheter into an outflow cannula of the implanted pump; expanding an expandable outflow member, thereby creating a seal between the outflow catheter and outflow cannula; flushing the implanted pump; collapsing the expandable members; and removing the catheters. These steps are preferably performed while the implanted pump is implanted within a human body. The flushing step may comprise flushing the implanted pump with a rinsing fluid; flushing the implanted pump with a thrombolytic fluid; and flushing the implanted pump with the rinsing fluid. The flushing step may comprise allowing the thrombolytic fluid to dwell in the implanted pump and/or agitating the thrombolytic fluid within the implanted pump. Expanding the expandable members preferably comprises causing a distal end thereof to extend distally and outwardly from the catheter, thereby forming a conical interior portion. This conical interior portion of the distal end of the catheter/expandable member assembly collects debris cleaned from the pump and prevents such debris from being trapped between the expandable member and the cannula.

FIG. 1 is an illustration of an implantable axial flow blood pump 10 for which the present invention may be particularly useful. The blood pump 10 may comprise a diffuser 1, a stator 2, an impeller 3, a flow straightener 4, an inflow cannula 5, and an outflow cannula 6 (best shown in FIG. 2), which may or may not have a flow meter 7 (best shown in FIG. 2) coupled therewith.

Figure 2:
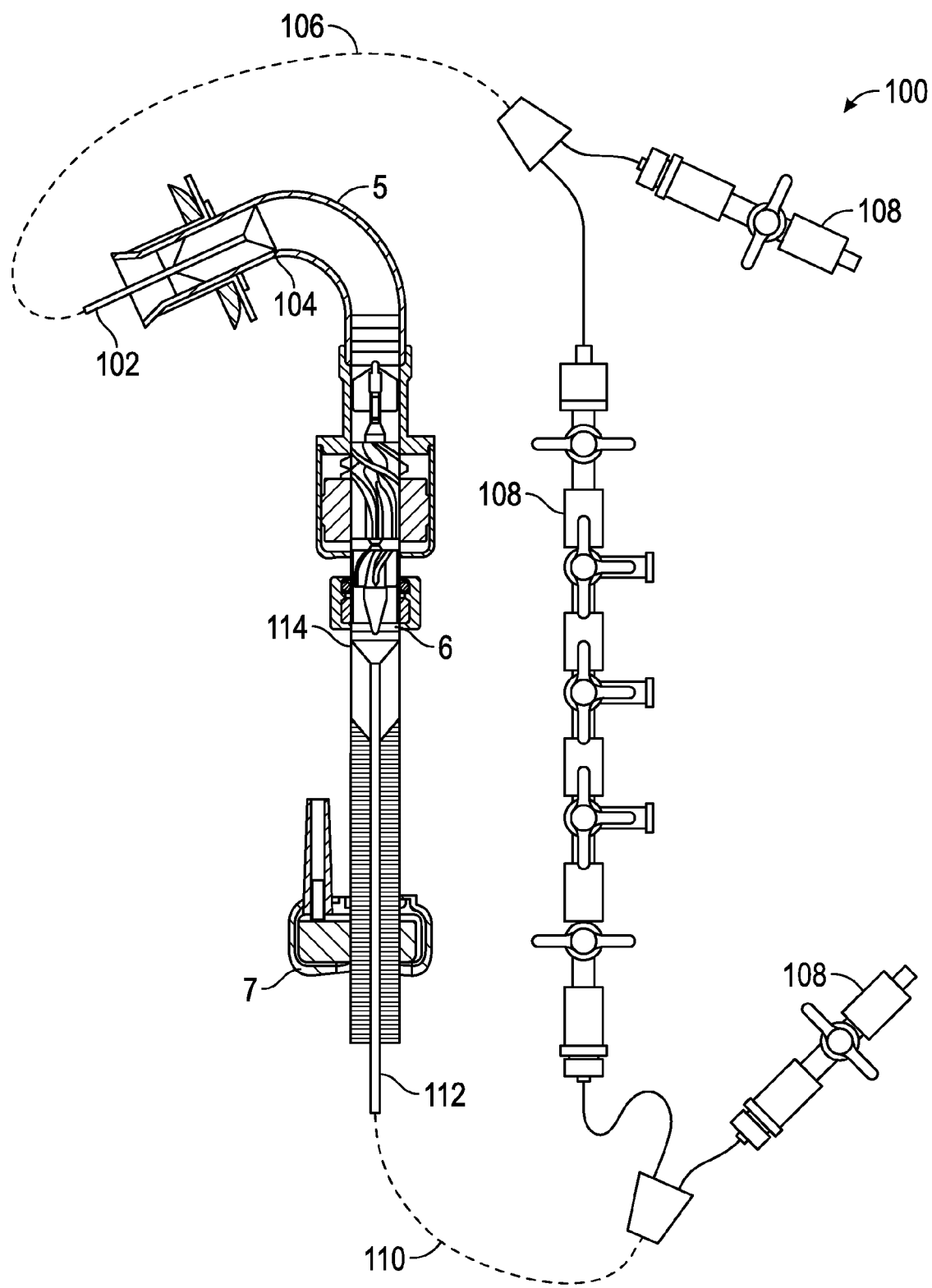
FIG. 2 illustrates a particular embodiment of a pump clean-out system utilizing certain aspects of the present inventions.

FIG. 2 is an illustration of a system 100 for cleaning an implanted blood pump, such as the pump 10. The system 100, according to the present invention, preferably comprises an inflow catheter 102 having an expandable inflow member 104 positioned about the periphery thereof; an inflow tube or lumen 106 coupled with the inflow catheter 102; a valve assembly 108 coupled to the inflow tube 106; an outflow tube or lumen 110 coupled to the valve assembly 108; and an outflow catheter 112 having an expandable outflow member 114 positioned about the periphery thereof, the outflow catheter 112 being coupled to the outflow tube 110.

The catheters 102 and 112 may be substantially conventional, such as 12-14 French Guide Catheters, and may be used with guide wires and/or introducers. The expandable members 104 and 114 are selectively expandable, once in place. Distal ends of the expandable members 104 and 114 preferably expand outwardly from the catheter to form a seal between the catheter and cannula of the implanted blood pump. As shown, when expanded, the expandable members 104 and 114 preferably form a conical distal end defined by a conical interior portion. The expandable members 104 and 114 may be relatively conventional balloons that are selectively inflated and deflated through a lumen, which may be integrated with the respective tubes 106 or 110 to form dual lumens.

The expandable members 104 and 114 may have structure to hold the shape of the conical distal end. For example, the expandable members 104 and 114 may have internal structure, such as that commonly used in many inflatable products, to hold the desired shape. The expandable members 104 and 114 may have strategically placed reinforced seams that assist in holding the desired shape. In any case, this conical interior portion of the distal end of the catheter/expandable member assembly is shaped and therefore acts like a funnel to collect debris cleaned from the pump and prevent such debris from being trapped between the expandable member and the cannula.

The valve assembly 108 is preferably a manifold assembly, as shown. Specifically, the valve assembly preferably includes isolation valves at either end, which allow the pump 10 to be isolated. The valve assembly 108 also preferably has one or more input valves to selectively allow rinsing fluid, such as a saline, and/or a Thrombolytic drug or fluid, such as a tissue plasminogen activator (TPA), to be flushed through the pump 10. The valve assembly 108 also preferably has one or more output valves to selectively allow the fluids to exit the system 110. The valve assembly may also include one or more inflator valves which selectively allow inflation and deflation of the expandable members 104 and 114.

In use, the tubes and/or lumens 106, 110 pass through the skin of a human body, with the catheters 102, 112 positioned within the human body and the valve assembly 108 positioned outside the human body. The fluid is passed through the inflow lumen 106 through the inflow catheter 102, through the pump 10, through the outflow catheter 112, and through the outflow lumen 110. Depending on the configuration of the valve assembly 108, the fluid may be circulated through the pump 10 repeatedly or only clean fluid may be introduced to the pump 10. This allows the present invention to clean out the implanted blood pump 10 without removing the pump 10 from the patient.

More specifically, the method of cleaning an implanted blood pump 10, the method preferably comprising the steps of: inserting an inflow catheter 102 into an inflow cannula 5 of the implanted pump 10; expanding an expandable inflow member 104, thereby creating a seal between the inflow catheter 102 and inflow cannula 5; inserting an outflow catheter 112 into an outflow cannula 6 of the implanted pump 10; expanding an expandable outflow member 114, thereby creating a seal between the outflow catheter 112 and outflow cannula 6; flushing the implanted pump 10; collapsing the expandable members 104, 114; and removing the catheters 102, 112. These steps are preferably performed while the implanted pump is implanted within a human body. After performing the steps, the pump 10 may be returned to normal service, without having been removed, thereby avoiding the pain, expense, and other issues related to removing and/or exchanging a pump for cleaning. This also allows the pump 10 to be cleaned more often, thereby increasing overall performance, reliability, and longevity of the pump 10.

The flushing step may also comprise allowing the thrombolytic fluid to dwell or soak in the implanted pump 10 and/or agitating the thrombolytic fluid within the implanted pump, such as by starting and stopping the pump 10. The flushing step may comprise flushing the implanted pump 10 with a rinsing fluid, such as a saline solution; flushing the implanted pump 10 with a thrombolytic fluid, such as TPA; and/or flushing the implanted pump 10 with the rinsing fluid, thereby flushing the TPA and any debris from the pump 10 before removing the system. It can be seen that the valve assembly 108 of the present invention allows the use of drugs and/or solvents that one would otherwise be hesitant to use in an implanted pump that was not isolated from the patient. Of course, without the present invention, such cleaning would normally be performed with the pump 10 removed from the patient. Thus, the present invention allows the pump to be cleaned effectively while the pump 10 remains within the patient.

Other and further embodiments utilizing one or more aspects of the inventions described above can be devised without departing from the spirit of Applicant's invention. Further, the various methods and embodiments of the present invention can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

What is claimed is:

1. A system for cleaning an blood pump configured to be implanted in a human body, comprising:
    an inflow catheter having an expandable inflow member positioned about the periphery thereof, the expandable inflow member being expanded outwardly from the inflow catheter forming a seal between the inflow catheter and an inflow cannula of the blood pump;
    an inflow tube coupled with the inflow catheter;
    a valve assembly coupled to the inflow tube;
    an outflow tube coupled to the valve assembly; and
    an outflow catheter having an expandable outflow member positioned about the periphery thereof, the outflow catheter being coupled to the outflow tube, the expandable outflow member being expanded outwardly from the outflow catheter forming a seal between the outflow catheter and an outflow cannula of the blood pump.

2. The system of claim 1, the expandable inflow member having a conical distal end defined by a conical interior portion.

3. The system of claim 1, further comprising an inflow lumen configured to allow selective inflation and deflation of the expandable inflow member.

4. The system of claim 3, wherein the inflow tube and inflow lumen are integrated into a dual inflow lumen assembly.

5. The system of claim 1, the expandable outflow member having a conical distal end defined by a conical interior portion.

6. The system of claim 1, further comprising an outflow lumen configured to allow selective inflation and deflation of the expandable outflow member.

7. The system of claim 6, wherein the outflow tube and outflow lumen are integrated into a dual outflow lumen assembly.

8. The system of claim 1, wherein the inflow tube and outflow tube are configured to extend through the skin of a human body, the inflow catheter and outflow catheter are configured to be, positioned within the human body, and the valve assembly is configured to be positioned outside the human body.

9. The system of claim 8, wherein the system is configured to define a fluid flow path from outside the human body, through the valve assembly, through the skin of the human body, through the inflow catheter, through the blood pump, through the outflow catheter, through the skin of the human body, and back to the valve assembly.

10. The system of claim 1, wherein the valve assembly includes isolation valves at either end.

11. The system of claim 1, wherein the valve assembly includes at least one input valve and at least one output valve to selectively allow a rinsing fluid to be circulated through the blood pump.

12. The system of claim 1, wherein the valve assembly includes at least one input valve and at least one output valve to selectively allow saline to be circulated through the blood pump, while the blood pump is within a human body.

13. The system of claim 1, wherein the valve assembly includes at least one input valve and at least one output valve to selectively allow a Thrombolytic fluid to be circulated through the blood pump, while the blood pump is within a human body.

14. The system of claim 1, wherein the valve assembly includes at least one input valve and at least one output valve to selectively allow a tissue plasminogen activator to be circulated through the blood pump, while the blood pump is within a human body.

15. The system of claim 1, wherein the valve assembly includes at least one inflator valve to selectively allow inflation and deflation of the expandable members.

16. The system of claim 1, wherein the system is configured to provides a fluid flow path into and out of a human body, thereby allowing the blood pump to be cleaned while the blood pump remains within the human body.

17. The system of claim 1, further including the implantable blood pump, wherein the blood pump is configured to pumps blood throughout a human body with the expandable members deflated and the blood pump is configured to pumps a rinsing fluid into and out of the human body with the expandable members inflated.

18. A system for cleaning an blood pump, comprising:
a blood pump configured to be implanted within a human body, the blood pump having an inflow cannula and an outflow cannula;
an inflow catheter having an expandable inflow member positioned about the periphery thereof, the expandable inflow member being configured to be positioned within the inflow cannula of the blood pump and within the human body, the expandable inflow member being expanded outwardly from the inflow catheter forming a seal between the inflow catheter and the inflow cannula of the blood pump;
an inflow tube coupled with the inflow catheter, the inflow tube being configured to extend through the skin of the human body;
a valve assembly coupled to the inflow tube, the valve assembly being configured to be positioned outside of the human body, the valve assembly including—
isolation valves at either end, and
at least one input valve and at least one output valve to selectively allow a rinsing fluid to be circulated through the implantable blood pump;
an outflow tube coupled to the valve assembly, the outflow tube being configured to extend through the skin of the human body; and
an outflow catheter having an expandable outflow member positioned about the periphery thereof, the outflow catheter being coupled to the outflow tube, the expandable outflow member being configured to be positioned within the outflow cannula of the blood pump and within the human body, the expandable outflow member being expanded outwardly from the outflow catheter forming a seal between the outflow catheter and the outflow cannula of the blood pump.

\* \* \* \* \*